United States Patent
Nagy et al.

(10) Patent No.: US 7,005,489 B2
(45) Date of Patent: Feb. 28, 2006

(54) ZWITTERIONIC METALLOCYCLES

(75) Inventors: Sandor Nagy, Naperville, IL (US); Mark P. Mack, West Chester, OH (US)

(73) Assignee: Equistar Chemicals, LP, Houston, TX (US)

( * ) Notice: Subject to any disclaimer, the term of this patent is extended or adjusted under 35 U.S.C. 154(b) by 253 days.

(21) Appl. No.: 10/673,896

(22) Filed: Sep. 29, 2003

(65) Prior Publication Data

US 2005/0070728 A1 Mar. 31, 2005

(51) Int. Cl.
*C08F 4/76* (2006.01)

(52) U.S. Cl. .............. 526/172; 526/134; 526/348; 556/51; 556/32; 556/7; 556/27; 556/30

(58) Field of Classification Search ............. 526/172, 526/161, 348.6, 348.2, 348.5, 351, 352, 257.9, 526/378.5, 170; 556/51, 736, 738, 30
See application file for complete search history.

(56) References Cited

U.S. PATENT DOCUMENTS

| | | | | |
|---|---|---|---|---|
| 5,153,157 A | 10/1992 | Hlatky et al. | ............... | 502/117 |
| 5,198,401 A | 3/1993 | Turner et al. | ............... | 502/155 |
| 5,241,025 A | 8/1993 | Hlatky et al. | ............... | 526/129 |
| 5,414,180 A | 5/1995 | Geerts et al. | ............... | 585/525 |
| 5,539,124 A | 7/1996 | Etherton et al. | ........... | 548/402 |
| 5,637,659 A | 6/1997 | Krishnamurti et al. | ...... | 526/133 |
| 5,648,440 A | 7/1997 | Sugano et al. | ............... | 526/132 |
| 5,902,866 A | 5/1999 | Nagy et al. | .................. | 526/133 |
| 6,211,311 B1 | 4/2001 | Wang et al. | ................. | 526/131 |
| 6,803,433 B1 * | 10/2004 | Lee | ............................. | 526/161 |
| 6,897,275 B1 * | 5/2005 | Wang et al. | ................ | 526/161 |

OTHER PUBLICATIONS

Shim et al. *J. Organomet. Chem.*, 2003, 675, 72-76.*
Thakkar et al. *J. Indian Chem. Soc.*, 1995, 55 421-423.*
Z. Komon et al., *J.Am.Chem.Soc.* 122 (2000) 1830.
B. Lee et al., *J.Am.Chem.Soc.* 123 (2001) 5352.
Y. Kim et al., *Organometallics* 21 (2002) 3082.
C. Lu et al., *J.Am.Chem.Soc.* 124 (2002) 5272.
J. Thomas et al., *J.Am.Chem.Soc.* 123 (2001) 5100.
Y. Kim et al., *Organometallics* 22 (2003) 1503.
B. Lee et al., *Organometallics* 21 (2002) 3481.
B. Lee et al., *Organometallics* 20 (2001) 5425.

* cited by examiner

*Primary Examiner*—David W. Wu
*Assistant Examiner*—Rip A. Lee
(74) *Attorney, Agent, or Firm*—John Tyrell; Jonathan L. Schuchardt

(57) ABSTRACT

A new class of zwitterionic metallocycles is disclosed. A positively charged Group 4-10 transition metal is chelated to two heteroatoms and one of the heteroatoms has a substituent bearing a negative charge. We have found that substitution in this position stabilizes the zwitterion form of the metallocycle. The zwitterionic metallocycle is useful for olefin polymerizations.

12 Claims, No Drawings

ZWITTERIONIC METALLOCYCLES

FIELD OF THE INVENTION

The invention relates to a new class of zwitterionic metallocycles. A positively charged Group 4-10 transition metal is chelated to two heteroatoms and one of the heteroatoms has a substituent bearing a negative charge. The zwitterionic metallocycle is useful for olefin polymerizations.

BACKGROUND OF THE INVENTION

While Ziegler-Natta catalysts are a mainstay for polyolefin manufacture, single-site (metallocene and non-metallocene) catalysts represent the industry's future. These catalysts are often more reactive than Ziegler-Natta catalysts, and they produce polymers with improved physical properties. These catalysts are typically formed by reacting an organometallic complex with an activator to produce an active catalyst wherein the metal develops a positive charge and the activator develops a negative charge.

Because of the many uses of metallocenes, there has been some effort to develop zwitterionic systems wherein both the positive and negative charges are in the same compound.

Metallocycles have been prepared where the negative-charged substituent is part of the metallocycle ring such as in the structure:

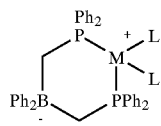

described by Peters et al. (*J. Am. Chem. Soc.* 124 (2002) 5272 and *J. Am. Chem. Soc.* 123 (2001) 5100) and studied for ethylene copolymerizations with carbon monoxide.

In *Organometallics* 22 (2003) 1503, zwitterionic zirconium complexes were used to polymerize ethylene. These complexes have the structure:

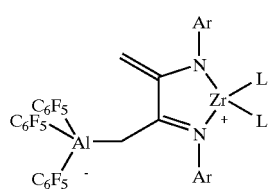

with the negative-charged substituent (a tetravalent aluminum compound) not being attached to the metallocycle at either of the nitrogen atoms.

Other zwitterionic compounds, where the negative-charged substituent is attached to the metallocycle at a point other than at one of the heteroatoms chelated to the metal, and their use in ethylene polymerizations include:

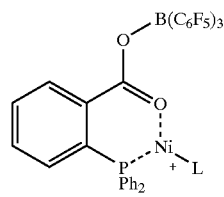

as reported in *J. Am. Chem. Soc.* 122 (2000) 1830 and:

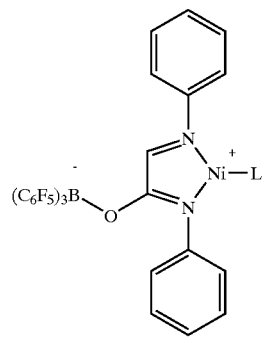

as reported in *J. Am. Chem. Soc.* 123 (2001) 5352, *Organometallics* 20 (2001) 5425 and *Organometallics* 21 (2002) 3082 and:

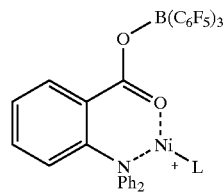

as reported in *Organometallics* 21 (2002) 3481.

None of these metallocycles has the substituent bearing the negative charge attached to one of the heteroatoms of the metallocycle.

SUMMARY OF THE INVENTION

The invention is a zwitterionic metallocycle useful for polymerizing olefins. The metallocycle is formed from a Group 4-10 transition metal chelated to two heteroatoms wherein one of the heteroatoms has a substituent bearing a full or partial negative charge and the transition metal bears a full or partial positive charge. The proximity of the substituent bearing a negative charge stabilizes the zwitterionic form versus the neutral metallocycle. Our modeling calculations suggest that when one of the heteroatoms has a substituent bearing a negative charge, the zwitterions are stabilized resulting in a large concentration of active sites available to catalyze olefin polymerizations.

DETAILED DESCRIPTION OF THE INVENTION

The invention is a zwitterionic metallocycle. The metallocycle comprises a Group 4-10 transition metal chelated to two heteroatoms wherein the two heteroatoms are each attached to a linking group and one of the heteroatoms has a substituent bearing a negative charge.

Preferred transition metals are Ti, Zr, Ni and Pt. The two heteroatoms are independently selected from the group consisting of P, N, O and S. Of these, N is preferred because the precursors are readily available. One of the heteroatoms has a substituent bearing a negative charge. Preferably, the negative charge is on an atom selected from the group consisting of B, Al, Sn and Sb. Of these, Al is most preferred because the zwitterionic metallocycle can be readily prepared from alkyl aluminum compounds.

By "zwitterionic" we mean that the metallocycle has some positive charge on the transition metal and some negative charge on the substituent. The charges need not be a full positive and a full negative charge, but can be a partial positive charge on the transition metal and a partial negative charge on the substituent.

The substituent bearing the negative charge is attached to one of the heteroatoms. The substituent bearing the negative charge is not attached at one of the other positions of the metallocycle, because these metallocycles favor the neutral form rather than the zwitterionic form.

The atom of the substituent that bears the negative charge may be directly bonded to the heteroatom or there may be one or more atoms separating the negatively charged atom from the heteroatom.

Suitable structures that have the atom bearing the negative charge directly bonded to the heteroatom include:

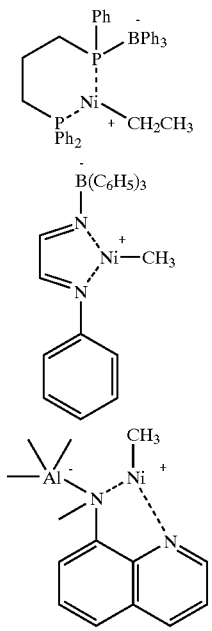

Suitable structures that have the atom bearing the negative charge separated by one or more atoms from the heteroatom include:

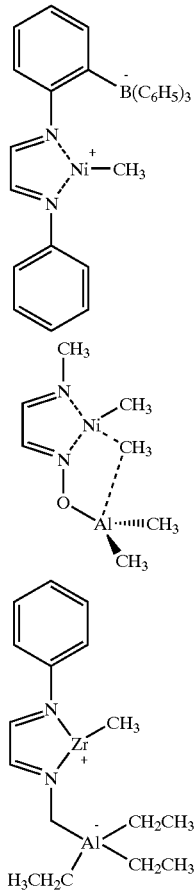

Unsuitable structures, with the substituent bearing the negative charge attached at one of the other positions of the metallocycle include:

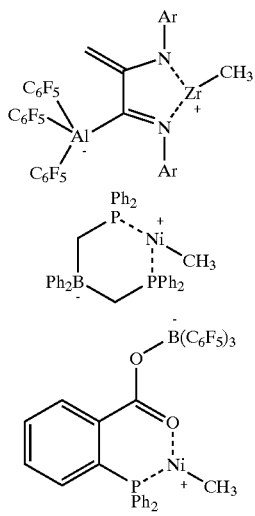

The two heteroatoms are each attached to a linking group to form a metallocycle. Preferably, the linking group comprises two substituted or unsubstituted $sp^2$-hybridized carbon atoms to form a 5-membered metallocycle.

Preferred metallocycles of the invention have the following general structure:

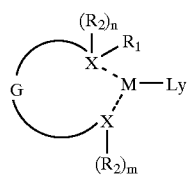

wherein M is a Group 4-10 transition metal bearing a full or partial positive charge, G is a linking group to form a metallocycle, each X is independently selected from the group consisting of P, N, O and S, each $R_2$ is independently selected from the group consisting of $C_1$–$C_{30}$ hydrocarbyl, m is 0, 1 or 2, n is 0 or 1, $R_1$ contains an atom bearing a full or partial negative charge selected from the group consisting of B, Al, Sn and Sb, L is independently selected from the group consisting of halide, alkoxy, siloxy, alkylamino, and $C_1$–$C_{30}$ hydrocarbyl and y satisfies the valence of M. Preferably, G comprises two substituted or unsubstituted $sp^2$-hybridized carbon atoms to form a 5-membered metallocycle. If an $sp^3$-hybridized carbon is present, the zwitterionic metallocycle may be too stable and not as reactive in olefin polymerizations.

A more preferred metallocycle has the general structure:

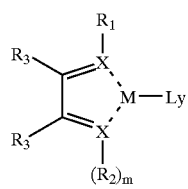

wherein M, X, L, $R_1$, $R_2$, and y are as defined above, each $R_3$ is independently selected from the group consisting of H and $C_1$–$C_{30}$ hydrocarbyl and m is 0 or 1.

Another preferred metallocycle has the general structure:

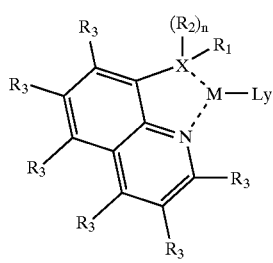

wherein M X, L, $R_1$, $R_2$, n, and y are as defined above and each $R_3$ is independently selected from the group consisting of H and $C_1$–$C_{30}$ hydrocarbyl.

The zwitterionic metallocycles can be made by several methods. One convenient method, illustrated in Examples 1 and 3, is to contact a ligand precursor containing the two heteroatoms attached to a linking group with a transition metal source. Any convenient source of the transition metal can be used to make the metallocycle. The transition metal source conveniently has labile ligands such as halide or dialkylamino groups that are easily displaced. Examples are halides (e.g., $TiCl_4$, $NiCl_2$, $ZrCl_4$), alkoxides, amides, and the like. After contact with the ligand precursor, the metallocycle is contacted with an alkyl aluminum, alkyl boron, alkyl tin or alkyl antimony source to introduce the substituent bearing the negative charge and to alkylate the transition metal, thereby forming the zwitterionic metallocycle in a single step.

The zwitterionic metallocycle can be used with a support such as silica, alumina, titania, or the like. Silica is preferred. The support is preferably treated thermally, chemically, or both prior to use to reduce the concentration of surface hydroxyl groups. Thermal treatment consists of heating (or "calcining") the support in a dry atmosphere at elevated temperature, preferably greater than about 100° C., and more preferably from about 150 to about 600° C., prior to use. A variety of different chemical treatments can be used, including reaction with organo-aluminum, -magnesium, -silicon, or -boron compounds. See, for example, the techniques described in U.S. Pat. No. 6,211,311, the teachings of which are incorporated herein by reference.

The zwitterionic metallocycle is particularly valuable for polymerizing olefins. Preferred olefins are ethylene and $C_3$–$C_{20}$ α-olefins such as propylene, 1-butene, 1-hexene, 1-octene, and the like. Mixtures of olefins can be used. Ethylene and mixtures of ethylene with $C_3$–$C_{10}$ α-olefins are especially preferred. The metallocycles can be used to copolymerize olefins with polar monomers such as carbon monoxide, vinyl silanes, vinyl acetates, acrylates and maleic anhydride. When a polar monomer is used, preferably ethylene is copolymerized with the polar monomer.

A wide variety of olefin polymerization processes can be used. Preferred processes are slurry, bulk, solution, and gas-phase proceses. A slurry or gas-phase process is preferably used. Suitable methods for polymerizing olefins are described, for example, in U.S. Pat. Nos. 5,902,866, 5,637,659, and 5,539,124, the teachings of which are incorporated herein by reference.

The polymerizations can be performed over a wide temperature range, such as about −30° C. to about 280° C. A more preferred range is from about 30° C. to about 180° C.; most preferred is the range from about 60° C. to about 100° C. Olefin partial pressures normally range from about 0.1 MPa to about 350 MPa. More preferred is the range from about 0.1 MPa to about 7 MPa.

Optionally, an additional activator is used in conjunction with the zwitterionic metallocycle. Suitable activators are well known in the art. Examples include alumoxanes (methyl alumoxane (MAO), PMAO, ethyl alumoxane, diisobutyl alumoxane), alkylaluminum compounds (triethylaluminum, diethyl aluminum chloride, trimethylaluminum, triisobutyl aluminum), and the like. Suitable activators include acid salts that contain non-nucleophilic anions. These compounds generally consist of bulky ligands attached to boron or aluminum. Examples include lithium tetrakis(pentafluorophenyl)borate, lithium tetrakis(pentafluorophenyl)aluminate, anilinium tetrakis(pentafluorophenyl)borate, and the like. Suitable activators also include organoboranes, which include boron and one or more alkyl, aryl, or aralkyl groups. Suitable activators include substituted and unsubstituted trialkyl and triarylboranes such as tris(pentafluorophenyl)borane, triphenylborane, tri-n-octylborane, and the like. These and other suitable boron-containing activators are described in U.S. Pat. Nos. 5,153, 157, 5,198,401, and 5,241,025, the teachings of which are incorporated herein by reference. Suitable activators also include aluminoboronates—reaction products of alkyl aluminum compounds and organoboronic acids—as described in U.S. Pat. Nos. 5,414,180 and 5,648,440, the teachings of which are incorporated herein by reference.

The optimum amount of activator needed relative to the amount of metallocycle complex depends on many factors, including the nature of the complex and activator, the desired reaction rate, the kind of polyolefin product, the reaction conditions, and other factors. Generally, however, when the activator is an alumoxane or an alkyl aluminum compound, the amount used will be within the range of about 0.01 to about 5000 moles, preferably from about 10 to about 500 moles, and more preferably from about 10 to about 200 moles, of aluminum per mole of transition metal, M. When the activator is an organoborane or an ionic borate or aluminate, the amount used will be within the range of about 0.01 to about 5000 moles, preferably from about 0.1 to about 500 moles, of activator per mole of M. The activator can be combined with the complex and added to the reactor as a mixture, or the components can be added to the reactor separately.

Metallocycle concentrations used for the olefin polymerization depend on many factors. Preferably, however, the concentration ranges from about 0.01 micromoles per liter to about 100 micromoles per liter. Polymerization times depend on the type of process, the catalyst concentration, and other factors. Generally, polymerizations are complete within several seconds to several hours.

The following examples merely illustrate the invention. Those skilled in the art will recognize many variations that are within the spirit of the invention and scope of the claims.

EXAMPLE 1

Preparation of Zwitterionic Metallocycle

To a stirring slurry of 1.30 g (0.01 mole) anhydrous $NiCl_2$ in 50 mL of hexane, 1.58 g (0.01 mole) 8-(methylamino) quinoline is added in portions over a period of twenty minutes. The mixture is allowed to stir overnight and 50 mL (0.1 mole) of trimethyl aluminum (2.0 M in hexane) is added over a period of 30 minutes. The expected active component is:

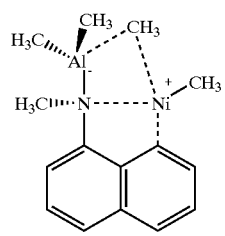

which is used "as is."

EXAMPLE 2

Ethylene Polymerization

A one-liter, stainless-steel reactor is charged with toluene (500 mL). The reactor is charged with ethylene to 2.4 MPa, and the contents are heated to 70° C. An aliquot of the hexane mixture (containing 2.0 mg of complex) from Example 1 is injected into the reactor to start the polymerization. Ethylene is supplied on demand to keep the reactor pressure constant at 2.4 MPa. After about 1 hour, the reactor is vented to recover polyethylene as the expected product.

EXAMPLE 3

Preparation of Zwitterionic Metallocycle

To a stirring slurry of 1.30 g (0.01 mole) anhydrous $NiCl_2$ in 50 mL of hexane, 0.86 g (0.01 mole) N-methyl-N'-hydroxyethanebisimine is added in portions over a period of twenty minutes. The mixture is allowed to stir overnight and 50 mL (0.1 mole) of trimethyl aluminum (2.0 M in hexane) is added over a period of 30 minutes. The expected active component is:

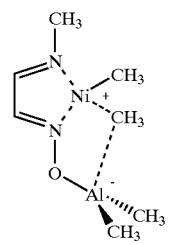

which is used "as is."

EXAMPLE 4

Ethylene Polymerization

A one-liter, stainless-steel reactor is charged with toluene (500 mL). The reactor is charged with ethylene to 2.4 MPa, and the contents are heated to 70° C. An aliquot of the hexane mixture (containing 2.0 mg of complex) from Example 3 is injected into the reactor to start the polymerization. Ethylene is supplied on demand to keep the reactor pressure constant at 2.4 MPa. After about 1 hour, the reactor is vented to recover polyethylene as the expected product.

Molecular Modeling Study

Additional evidence for the suitability of metallocycles as catalysts comes from molecular modeling studies. We make two calculations. The first is to see whether the neutral form or the zwitterion form is preferred. The more the zwitterion form is preferred, the higher the concentration of catalytically active sites. The second calculation is to look at the interaction of the zwitterion with ethylene to form a pi-complex. The zwitterion should be stable enough to be preferred versus the neutral form yet not so stable that it fails to react with ethylene. All calculations are performed with complete geometry optimization using the DFT model B3LYP with the LACVP** pseudopotential basis set as incorporated into the TITAN™ software package. We initially perform calculations with the complex from Example 1.

A
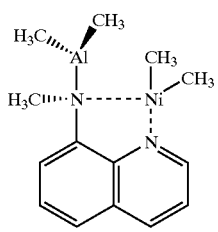

B
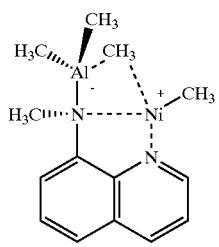

The calculations (DFT, B3LYP) indicate that the polarized (zwitterionic) species (B) involving a bridging methyl group is energetically more favorable than structure (A), resulting in a high concentration of catalytically active sites.

The zwitterion has an exothermic interaction of the metal center with ethylene resulting in formation of a pi-complex, which is considered to be a rate-limiting step in the polymerization process. The calculated pi-complexation energy is −4 kcal/mol, indicating that it is a favorable reaction step.

The complex from Example 3 is also studied. The calculations (DFT, B3LYP) indicate that the polarized (zwitterionic) species involving a bridging methyl group is the energetically favored structure, resulting in a high concentration of catalytically active sites. The calculated pi-complexation energy is −6 kcal/mol, indicating that it is a favorable reaction step.

For comparative purposes, calculations are performed on other complexes where neither of the heteroatoms of the metallocycle contains a substituent bearing a negative charge.

Comparative Complex A
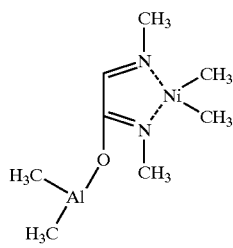

Comparative Complex B
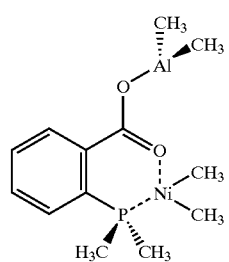

Comparative Complex A is similar in structure to the complex from Example 3, but the negative charge cannot form on a substituent attached to one of the heteroatoms. This turns out to be a critical difference. The calculated (DFT, B3LYP) stabilization of the inactive neutral system is 4 kcal/mol. In other words, the energy state of the zwitterion is 4 kcal/mol higher than the neutral form. This indicates that the polarized (zwitterionic) species is energetically disfavored relative to the neutral form, resulting in a low concentration of catalytically active sites. For Comparative Complex B, the calculated (DFT, B3LYP) stabilization of the inactive neutral system is 9 kcal/mol. This indicates that the polarized (zwitterionic) species is energetically disfavored (9 kcal/mol higher energy than the neutral form), resulting in a low concentration of catalytically active sites.

Calculations are also performed on Complex C, which includes an $sp^3$-hybridized carbon as part of the linking group forming the metallocycle.

Complex C
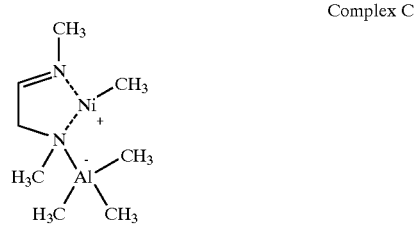

The calculations (DFT, B3LYP) indicate that the polarized (zwitterionic) species is the energetically favored structure, resulting in a high concentration of catalytically active sites. However, the calculated pi-complexation energy with ethylene is 4 kcal/mol, indicating that Complex C is overly stabilized and that it is preferable for the linking group to contain $sp^2$ carbons.

The modeling data shows that metallocycles with a heteroatom having a substituent capable of bearing a negative charge favor formation of the zwitterion. Since it is the zwitterion that complexes with the olefin, these metallocycles should be more catalytically active. The data also show that zwitterionic metallocycles of the invention have favorable pi-complexation energies, indicating this as a favorable reaction step.

The preceding examples are meant only as illustrations. The following claims define the invention.

The invention claimed is:

1. A zwitterionic metallocycle comprising a Group 4-10 transition metal chelated to two heteroatoms independently selected from the group consisting of P, N, O, and S wherein the two heteroatoms are each attached to a linking group to form a metallocycle and wherein one of the heteroatoms has a substituent bearing a full or partial negative charge on atom selected from the group consisting of B, Al, Sn and Sb and wherein said atom is directly bonded to the heteroatom and the transition metal has a full or partial positive charge.

2. A zwitterionic metallocycle of general formula:

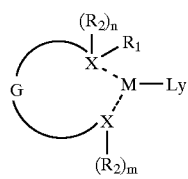

wherein M is a Group 4-10 transition metal bearing a full or partial positive charge, G is a linking group to form a metallocycle and comprises two substituted or unsubstituted sp$^2$ carbon atoms to form a 5-membered metallocycle; each X is independently selected from the group consisting of P, N, O and S, each $R_2$ is independently selected from the group consisting of $C_1$–$C_{30}$ hydrocarbyl, m is 0, 1 or 2, n is 0 or 1, $R_1$ contains an atom bearing a full or partial negative charge selected from the group consisting of B, Al, Sn and Sb, L is independently selected from the group consisting of halide, alkoxy, siloxy, alkylamino, and $C_1$–$C_{30}$ hydrocarbyl and y satisfies the valence of M.

3. The zwitterionic metallocycle of claim 2 wherein X is N and $R_1$ contains an atom bearing a full or partial negative charge selected from the group consisting of B and Al.

4. The zwitterionic metallocycle of claim 2 having the general formula:

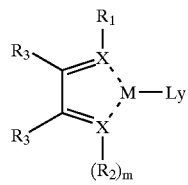

wherein each $R_3$ is independently selected from the group consisting of H and $C_1$–$C_{30}$ hydrocarbyl and m is 0 or 1.

5. The zwitterionic metallocycle of claim 2 having the general formula:

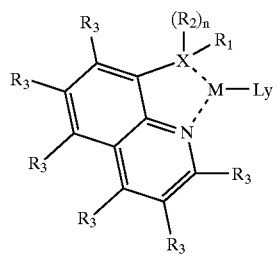

wherein each $R_3$ is independently selected from the group consisting of H and $C_1$–$C_{30}$ hydrocarbyl.

6. An olefin polymerization process comprising contacting an olefin with a zwitterionic metallocycle comprising a Group 4-10 transition metal chelated to two heteroatoms independently selected from the group consisting of P, N, O, and S wherein the two heteroatoms are each attached to a linking group to form a metallocycle, and wherein one of the heteroatoms has a substituent bearing a full or partial negative charge on an atom from the group consisting of B, Al, Sn and Sb and wherein said atom is directly bonded to the heteroatom and the transition metal bears full or partial positive charge.

7. The olefin polymerization process of claim 6 wherein the olefin is selected from the group consisting of ethylene, propylene, 1-butene, 1-hexene, 1-octene and mixtures thereof.

8. The olefin polymerization process of claim 6 wherein the olefin is copolymerized with a polar comonomer.

9. The olefin polymerization process of claim 8 wherein the olefin is ethylene and the polar comonomer is selected from the group consisting of carbon monoxide, vinyl silanes, vinyl acetates, acrylates and maleic anhydride.

10. The olefin polymerization process of claim 6 wherein the zwitterionic metallocycle is supported.

11. A slurry olefin polymerization process of claim 6.

12. A gas-phase olefin polymerization process of claim 6.

* * * * *